United States Patent [19]

Bailey et al.

[11] Patent Number: 4,863,875

[45] Date of Patent: Sep. 5, 1989

[54] DYE LABELLED ANTIBODIES AS REAGENTS FOR USE IN IMMUNOASSAY SYSTEMS

[75] Inventors: Anne Bailey, Wayne; Andrejs Rasums, Hamilton Square, both of N.J.

[73] Assignee: GIA Research Company, L.P., New York, N.Y.

[21] Appl. No.: 769,589

[22] Filed: Aug. 26, 1985

[51] Int. Cl.$^4$ ............... G01N 33/533; G01N 33/543
[52] U.S. Cl. .................................. 436/518; 436/531; 436/536; 436/537; 436/546; 436/800; 436/808; 436/810; 436/815; 530/387; 530/402; 530/405; 530/409
[58] Field of Search ............... 436/518, 531, 536, 537, 436/546, 800, 808, 810, 815; 530/387, 402, 405, 409

[56] References Cited

U.S. PATENT DOCUMENTS

| | | |
|---|---|---|
| 4,152,411 | 5/1979 | Schall, Jr. .......................... 436/800 |
| 4,232,119 | 11/1980 | Carlsson et al. . |
| 4,331,590 | 5/1982 | Boguslaski et al. . |
| 4,379,135 | 4/1983 | Sasaki et al. . |
| 4,404,289 | 9/1983 | Masuda et al. . |
| 4,405,711 | 9/1983 | Masuda et al. . |
| 4,434,150 | 2/1984 | Azad et al. . |
| 4,435,509 | 3/1984 | Berthold et al. ..................... 436/518 |
| 4,452,886 | 6/1984 | Henry .................................. 436/544 |
| 4,473,652 | 9/1984 | Okazaki et al. . |
| 4,491,634 | 1/1985 | Frenzel . |
| 4,503,143 | 3/1985 | Gerber et al. . |
| 4,511,478 | 4/1985 | Nowinski et al. ................... 436/531 |
| 4,605,630 | 8/1986 | Kung et al. ......................... 436/511 |
| 4,609,707 | 9/1986 | Nowinski et al. ................... 436/531 |
| 4,711,840 | 12/1987 | Nowinski et al. ................... 436/501 |

Primary Examiner—Christine M. Nucker

[57] ABSTRACT

Reagents qualitatively and quantitatively measure ligands such as antigens and haptens in biological fluids. The reagents include at least ten dye molecules or at lead one dye polymer having at least ten dye monomers per polymer bound to an antibody through an isothiocyanate group on the dye.

38 Claims, No Drawings

DYE LABELLED ANTIBODIES AS REAGENTS FOR USE IN IMMUNOASSAY SYSTEMS

BACKGROUND OF THE INVENTION

The present invention is directed to new reagents for the qualitative and quantitative measurement of ligands such as antigens and haptens in biological fluids. The reagents are comprised of at least ten dye molecules or at least one dye polymer having at least ten dye monomers per polymer bonded to an antibody through an isothiocyanate group on the dye.

Dye molecules have been used as labels for proteins (e.g. antibodies) to make reagents which have been primarily associated with fluorescence readings. It is generally accepted that labeling an antibody with a dye molecule and measuring the absorbance value does not provide a level of sensitivity sufficient to enable an accurate quantitative measurement of ligands in immunoassay systems. This is because there are obstacles to obtaining a sufficiently sensitive reagent whose change in absorbance values can be accurately measured by standard equipment such as a spectrophotometer or by the naked eye. (See "Labeling of Proteins with Fluorescent Dyes" J. J. Haaijman, *Immunohistochemistry* Edited by A. C. Cuello pp. 47-85, 1983)

To obtain a sufficiently sensitive dye-labeled antibody reagent, it is necessary to create reagents having a sufficient number of dyes bound to each antibody to provide maximum absorbance.

Dye molecules which have a relatively high molar extinction coefficient value ($\epsilon$) increase sensitivity. Dye molecules satisfy this requirement are known in the art and include isothiocyanate derivatives of aminofluorescein and aminophthalocyanines as well as Chicago Sky Blue and Evans Blue. The molar extinction coefficient value ($\epsilon$) is a measure of the optical density of the dye at a one molar concentration measured at the maximum absorbance peak. The greater the number of optical density units per molar solution, the higher the level of sensitivity of the dye.

The art has not been successful in producing a reagent having a sufficient number of dyes bound to each antibody to provide a sensitive reagent for immunoassay testing.

Prior to the present invention it was believed that the number of dyes which could be bound to an antibody must be limited so as to avoid having the dyes interfere with the binding sites on the antibody for binding to the ligand to be detected.

Highly over-conjugated antibodies tend to decrease antibody activity which makes quantitative measurement difficult. Therefore, the art has limited the number of dyes bound to a protein (e.g. antibodies) (see *Immunohistochemisty* p. 56 showing four dye molecules bound to a protein; and U.S. Pat. No. 4,261,968, column 25, lines 35-40 showing a maximum of nine dye molecules per antibody molecule).

However, such prior art reagents are not sensitive enough for use in immunoassay procedures for the quantitative measurements of ligands, especially tests on serum samples containing low concentrations of antigens and haptens and for visual tests without the aid of absorbance measuring equipment.

It is therefore an object of the present invention to provide a sensitive reagent for use in immunoassay procedures wherein the reagent comprises at least ten dye molecules or at least one dye polymer having at least ten dye monomers per polymer bound to an antibody through an isothiocyanate group on the dye molecule or polymer.

It is another object of the invention to provide methods of making such reagents.

It is a further object of the invention to employ these reagents in immunoassay tests for the qualitative and quantitative detection of ligands in biological fluids.

It is a still further object of the invention to provide immunoassay procedures for qualitatively and quantitatively detecting the presence of Apoprotein A-1 in serum samples.

SUMMARY OF THE INVENTION

The present invention is directed to reagents for use in immunoassay procedures for the qualitative and quantitative detection of ligands (e.g. antigens and haptens) in biological fluids and to methods of making the reagents. The reagents comprise at least ten dye molecules or at least one dye polymer having at least ten, preferably between about 40 and 200 dye monomers per polymer, bound to an antibody through an isothiocyanate group on the dye molecule or polymer. It is preferred that the number of dye polymers is from 1 to 10, most preferably from 1 to 3.

The dye molecules and polymers employed as part of the reagent have an isothiocyanate group for binding to the antibody. The dye molecules and polymers should have a molar extinction coefficient value ($\epsilon$) in the range of at least 50,000, preferably from 50,000 to 20,000. As previously indicated, the ($\epsilon$) value is the optical density value of a dye solution made at a one molar concentration and is normally measured at the maximum absorbance value. It calculated in accordance Beer-Lambert's Law.

The dye molecules should have a structure which is not significantly hindered by chemical groups proximal to the dye on the antibody, to avoid having the ($\epsilon$) value of the dye significantly decrease when bound to the antibody.

Dye molecules particularly suited for use in making the reagents of the present invention are fluorescein isothiocyanate ($\epsilon = 60,000$), isothiocyanate derivatives of aminophthalocyanines ($\epsilon = 120,000$ to 220,000), Chicago Sky Blue ($\epsilon = 61,000$) and Evans Blue ($\epsilon = 50,000$). Fluorescein isothiocyanate (FITC) is particularly preferred. The aminophthalocyanines which are employed as starting materials for the dye molecules can be converted to isothiocyanate derivatives by reaction with thiophosgene in a manner known in the art.

Dye polymers may also be employed in the present invention and include polymers of the dye molecules mentioned above including a polymer having a fluorescein moiety. The preparation of such polymers is disclosed in U.S. Pat. No. 4,452,886 incorporated herein by reference, and specifically to the first class of polymers disclosed therein. Such polymers may have at least one free amino group which can be converted to an isothiocyanate group by reaction with, for example, thiophosgene. More specifically, the dye polymers employed in the present invention are water-soluble polymers having at least ten, preferably between about 40 and 200 dye monomers wherein at least one of the dye monomers has a free isothiocyanate group for binding to the antibody of the reagent.

The antibodies which may be used as part of the reagent are virtually unlimited and include any antibody which may be bound by at least ten dye molecules or the dye polymers as described above and which has at least one binding site for the ligand to be detected.

The reagents have at least 10 dyes bound to the antibody, preferably about 15 to about 40 dye molecules per antibody, most preferably 20 to 35 dye molecules per antibody. The reagent incorporating dye molecules therefore has a dye/protein (D/P) molar ratio of at least 10, preferably 15–40 and most preferably 20–35 As previously indicated, the number of dye polymers per antibody is preferably 1 to 10, most preferably 1 to 3. Such reagents can quantitatively detect ligands having a concentration of about ⅓ the minimum concentration employing previous dye llabeled antibodies.

The sensitivity of the present reagents can be evaluated based on the degree of specific absorbance which is the quantity of optical density (O.D.) per weight unit of antibody. A labeled antibody having a D/P ratio of 30 has a specific absorbance of 13 milliabsorbance units per microgram. In order to observe a difference in the amount of absorbance there must be a change of approximately 20 milliabsorbance units. Accordingly, when using antibody against IgG for example, the amount of labeled antibody necessary to observe a change in absorbance will be 1.5 micrograms (20 mA ÷ 13 mA/microgram). Assuming that the volume of the sample is 100 microliters, then the present reagents are able to measure an IgG concentration of about 15 micrograms/ml. The present reagent is therefore sufficiently sensitive to measure many different analytes.

The dyes employed in the present invention absorb photons in the visible or UV spectrum. The dyes typically contain chromogenic groups which absorb photons of specific wavelengths in the visible or UV region. Auxochromic groups which are functional groups such as ——SH, ——OH, and ——NR$_2$ where R is hydrogen or lower alkyl change the wavelength at which photons are absorbed. Usually the presence of these groups results in absorption at a higher wavelength.

The ligands which can be detected by employing the present reagent include those having a molecular weight in the range of from about 100 to several million. The term "ligand" is used in its customary broad sense and includes for example, drugs, hormones, apoproteins including Apoprotein A-1, proteins, vitamins, viruses, bacteria and enzymes.

The reagents of the present invention are particularly suited for the detection of Apoprotein A-1 which is one of about 500 specific proteins which circulate in the blood. It is generally recognized that patients with low levels of this lipoprotein have a relatively high risk of cardiovascular disorders. It is desirable to employ a dye/protein (D/P) molar ratio of 25 to 30 when making a reagent for detecting the presence of Apoprotein A-1 using FITC.

The reagents may be prepared by adding a solution of the dye molecules or dye polymer to the antibody at a molar ratio (D/P) of at least 100:1, preferably 130:1 to 300:1 for a time sufficient to enable the antibody and dyes to bind, typically for up to three hours. With respect to the dye polymers, the above molar ratio (D/P) values pertain to the dye polymers per se and not to the dye monomers which make up the dye polymers.

The reaction is conducted at ambient temperature such as about 25° C. The concentration of antibody is limited only by the molar ratio (D/P) of dye molecules or polymers to antibody but is conveniently employed at about 1.5 to 2.5 mg/ml.

An alternative method of producing the reagent comprises using higher temperatures (i.e. 30°–45° C.) preferably about 37° C. which has the effect of reducing the reaction time to between 30 and 90 minutes although up to 3 hours may be used if desired.

The reagents may be used in solid phase separation procedures such as direct and reverse sandwich procedures which are examples of heterogeneous immunoassay systems.

More specifically, in a reverse sandwich procedure the sample containing the ligand (e.g., antigen) to be detected is reacted with the reagent containing antibody to the ligand to form a complex wherein the ligand of the sample binds to the antibody of the reagent. A solid phase support comprising a substrate (e.g. CNBr activated Sepharose 4B manufactured by Pharmacia Fine Chemicals) bound to antibody to the ligand is added to the complex to form a second complex and a supernatant containing unbound reagent. The second complex arises because of the binding of the ligand of the first complex to the antibody bound to the solid phase.

The second complex is then separated from the supernatant. Thereafter a measurement is taken of the amount of absorbance of photons of the supernatant containing unreacted reagent which amount is compared with the amount of absorbance of a standard solution containing a known amount of ligand.

A direct sandwich procedure provides for the combination of the ligand to be detected with antibody to the ligand bound to the solid phase wherein the ligand binds to the antibody of the solid phase to form a first complex. Then the reagent is added to the first complex and a second complex is formed with the ligand of the first complex binding to the antibody of the reagent. The same separation and measurement procedures are then employed as in the reverse sandwich method.

The following examples set forth preferred embodiments of the present invention and are not intended to limit the scope of the invention described in the claims annexed hereto.

EXAMPLE 1

Preparation of FITC - Antibody to Apoprotein A-1

Purified antibody against apoprotein A-1 was dialyzed 0.05M of NaCl. To this solution, 0.5M of sodium bicarbonate (pH 9.5) was added to obtain a 0.15–0.20M solution at pH 9.5.

50 ml of the antibody solution was placed in a water bath at 37° C. for 20 minutes. At the same time 43.3 mg of fluorescein isothiocyanate (FITC) was dissolved in 300 microliters of dimethyl formamide and the resulting solution was immediately added to the antibody solution under stirring. Stirring of the combined solution was continued for 35 minutes. The amount of FITC added to the antibody solution equivalent to a molar ratio of FITC/Antibody of 130.

After stirring of the combined solution was completed, the reaction vessel was removed from the water bath and the combined solution was loaded on a Sephadex G25 column ($\phi$=22 mm; L=70 cm) and eluted with 0.05M TRIS buffer at a pH of 8.4. The resulting FITC labeled antibody appeared as the first peak in the void volume of the column.

The D/P ratio of the labeled antibody was calculated according to the method described in *Immunohisto-*

*chemistry* at page 79 by taking absorbance readings at 280 nm and 495 nm.

EXAMPLE 2

Preparation of FITC-Antibody to Apoprotein A-1

50 ml of the same antibody solution used in Example 1 was placed in a water bath at ambient temperature (about 25° C.). 60 mg of FITC was dissolved in 300 microliters of dimethyl formamide and the dye solution was immediately added to the antibody solution under stirring. Stirring was continued for 180 minutes. The amount of FITC added to the antibody solution provided a FITC/Antibody ratio in the combined solution of 180:1.

Thereafter the reaction vessel was removed from the water bath and the combined solution was loaded on a Sephadex G25 column ($\phi=22$ mm; L=70 cm) and eluted with 0.05M TRIS buffer pH of 8.4. The resulting FITC labeled antibody appeared as the first peak in the void volume of the column.

The FITC/antibody ratio of the final product was determined in the same manner as Example 1.

EXAMPLE 3

Measurement of Preserved Antibody Activity

The preparation of FITC-Antibody to Apoprotein A-1 reagent as described in Examples 1 and 2 was repeated using antibody concentrations of from 1.5 to 2.5 mg/ml to provide eight additional reagents (Samples 3-11) under the conditions set forth in Table 1.

The percent of antibody activity remaining after binding of FITC to the antibody was determined in the following manner.

The antibody activity of the FITC labeled antibody was compared to the activity of the same, unlabeled antibody. This activity was measured by allowing both antibodies to react with Apoprotein A-1 bound to the solid phase.

A solid phase support of CNBr activated Sepharose 4B bound to Apoprotein A-1 was prepared according to the procedure described by Pharmacia Fine Chemicals product catalog 1974 edition. A second solid phase made of antibody bound sepharose was used to establish non-specific binding values.

The unlabeled antibody solution was diluted with a buffer containing/ 0.05M TRIS and 0.4% TWEEN. An absorbance reading was taken of the unlabeled antibody solution at 280 nm.

In a separate vessel, 0.4 ml of the Apoprotein A-1 sepharose gel was washed with one ml of the same assay buffer. The resulting supernatant was discarded. 1.3 ml of the resulting diluted antibody solution was added to the sepharose gel and incubated at room temperature under agitation for 30 minutes.

The resulting mixture was centrifuged to produce a supernatant which was measured for absorbance using a spectrophotometer at 280 nm.

A solution of antibody labeled with FITC was diluted and reacted with an Apoprotein A-1 bound solid phase in the same manner as the unlabeled antibody. The buffer used was 0.15M TRIS, 0.4% TWEEN and 0.4% bovine serum albumin (BSA). Absorbance readings were taken at 95 nm.

The degree of preserved antibody activity of the FITC labeled antibody as compared to the unlabeled antibody is set forth in Table I as a percent of activity based on the activity of the unlabeled antibody.

The same procedures were carried out for each of samples 1-11 and the results are shown in Table I.

Table I shows that a reagent having a D/P ratio falling within the present invention retains antibody binding activity to a sufficient extent (as high 90.7%) so that the reagent can be used effectively in immunoassay tests. Table I further shows that employing a high D/P ratio in the initial reaction mixture results in a relatively high D/P ratio in the resulting reagent. Furthermore, increasing the reaction temperature above ambient temperature aids in the formation of a reagent having a high D/P ratio.

TABLE I

| Sample | Reaction Time | Reaction Temperature | D/P molar ratio in reaction mixture | D/P ratio in product | % of preserved antibody reactivity |
|---|---|---|---|---|---|
| 1 | 35 min. | 37° C. | 130 | 28.2 | 90.7 |
| 2 | 180 min. | 25° C. | 180 | 24.2 | 83.8 |
| 3 | 180 min. | 25° C. | 180 | 20.0 | 77.7 |
| 4 | 180 min. | 25° C. | 130 | 22.6 | 80.1 |
| 5 | 180 min. | 25° C. | 300 | 33.6 | 47.8 |
| 6 | 35 min. | 37° C. | 130 | 26.4 | 79.1 |
| 7 | 90 min. | 37° C. | 130 | 30.0 | 68.7 |
| 8 | 90 min. | 37° C. | 130 | 32.0 | 65.1 |
| 9 | 180 min. | 37° C. | 130 | 33.4 | 59.4 |
| 10 | 35 min. | 37° C. | 180 | 32.3 | 55.8 |
| 11 | 35 min. | 37° C. | 300 | 36.6 | 43.2 |

EXAMPLE 4

Reserve Sandwich Assay For the Detection of Apoprotein A-1

20 microliters of a serum sample containing an unknown amount of Apoprotein A-1 was added to 1.3 ml of an assay buffer containing 0.15M TRIS, 0.4% of BSA and 0.4% of TWEEN 20 and allowed to stand for 15 minutes. 250 microliters of the buffered solution were added to a series of test tubes. 250 microliters of a FITC-labeled antibody solution containing 75 micrograms of affinity-purified antibody against Apoprotein A-1 was added to each of the tubes.

The tubes were then transferred to a water bath heated to 37° C. and incubated for 30 minutes.

A solid phase support prepared in the same manner as Example 3 except that antibody against Apoprotein A-1 instead of Apoprotein A-1 was coupled to agarose gel to form a solid phase compressed into tablet form. Each tablet contained 500 microliters of wet gel and 800 micrograms of the antibody. The thus prepared solid phase bound to antibody against Apoprotein A-1 was added to each of the incubated tubes and the tubes were incubated again for 60 minutes in a water bath maintained at 37° C.

Thereafter, 1.3 ml of the assay buffer described above was added to each of the tubes and vortexed to thoroughly mix the reaction products. The resulting mixture was subjected to centrifugation to produce a complex and a supernatant containing unreacted reagent. The supernatant was removed from the tubes and read on a spectrophotometer at 495 nm (peak value) and 600 nm (background) to obtain an absorbance value. The absorbance value was compared with the absorbance values of standard solutions containing known amounts of Apoprotein A-1 to obtain the concentration of Apoprotein A-1 in each of the serum samples.

EXAMPLE 5

Direct Sandwich Assay For the Detection of Apoprotein A-1

An agarose gel solid phase support having 2 mg of antibody against Apoprotein A-1 bound thereto was prepared in the same manner as Example 4. To each of several tubes containing 0.6 ml of the above prepared solid phase was added one ml of a buffered serum sample containing 2 microliters of serum having an unknown quantity of Apoprotein A-1. The buffer used for the serum sample was the same as employed in Example 4.

The tubes were set on a shaker for 30 minutes at room temperature. Thereafter the tubes were centrifuged and decanted. 3 ml of buffer was added to each of the tubes which were then mixed and centrifuged and decanted again.

1.2 ml of a FITC labeled antibody solution containing 96 micrograms of antibody against Apoprotein A-1 was added to each of the tubes followed by shaking on a shaker for 30 minutes. The reaction product was then centrifuged and the supernatant removed and measured for absorbance in a spectrophotometer at 495 nm.

What we claim is:

1. A reagent for the detection in biological fluids of a liquid comprising:
   an antibody to said ligand bound to more than 10 dye molecules through an isothiocyanate group on the dye molecule.
2. The reagent of claim 1 wherein the antibody of said reagent is bound to 15 to 40 of said dye molecules.
3. The reagent of claim 2 wherein the antibody of said reagent is bound to 20 to 35 of said dye molecules.
4. The reagent of claim 1 wherein the ligand to be detected is Apoprotein A-1.
5. The reagent of claim 1 wherein said dye molecule has molar extinction coefficient of at least 50,000.
6. The reagent of claim 5 wherein said dye molecule has a molar extinction coefficient of 50,000 to 220,000.
7. The reagent of claim 6 wherein said dye molecules are selected from the group consisting of isothiocyante derivatives of aminofluorescein and aminophthalocyanines, Chicago Sky Blue and Evans Blue.
8. The reagent of claim 7 wherein said dye molecule is flourescein isothiocyanate.
9. A reagent for the detection in biological fluids of Apoprotein A-1 comprising an antibody to Apoprotein A-I bound to 25 to 30 molecules of fluorescein isothiocyanate.
10. A process for the preparation of a reagent useful for the detection of a ligand in a biological fluid, said reagent comprising an antibody to said ligand bound to more than 10 dye molecules through an isothiocyanate group on said dye molecule, said method comprising:
   (a) combining said dye molecules with said antibody at a molar ratio of at least 100:1 at ambient temperature for a time sufficient to enable said antibody to bind to said dye molecules to thereby form said reagent.
11. The process of claim 10 wherein the antibody of said reagent is bound to 15 to 40 of said dye molecules.
12. The process of claim 11 wherein the antibody of said reagent is bound to 20 to 35 of said dye molecules.
13. The process of claim 10 wherein the molar ratio of said dye molecules to said antibody is from 130:1 to 300:1.
14. The process of claim 10 wherein said dye molecules are selected from the group consisting of isothiocyanate derivatives of aminofluorescein and aminophthalocyanines, Chicago Sky Blue and Evans Blue.
15. The process of claim 10 wherein said dye molecule is fluorescein isothiocyanate.
16. A process for the preparation of a regent useful for the detection of a ligand in a biological fluid, said reagent comprising an antibody to said ligand bound to more than 10 dye molecules through an isothiocyanate group on the dye molecule, said method comprising reacting said antibody and said dye molecules at a temperature of between about 30° and 45° C. for a time sufficient to enable said antibody to bind to said dye molecules to form said reagent.
17. The process of claim 16 wherein the dye molecules and antibody are reacted at a molar ratio of at least 100:1.
18. The process of claim 17 wherein the molar ratio of dye molecules to antibody is from 130:1 to 300:1.
19. The process of claim 16 wherein the antibody of said reagent is bound to 15 to 40 of said dye molecules.
20. The process of claim 19 wherein the antibody to said reagent is bound to 20 to 35 of said dye molecules.
21. The process of claim 16 wherein said dye molecule are selected from the group consisting of isothiocyante derivatives of aminofluorescein and aminophthalocyanines, Chicago Sky Blue and Evans Blue.
22. The process of claim 21 wherein said dye molecule is fluorescein isothiocyante.
23. The process of claim 16 wherein the reaction temperature is about 37° C.
24. A process for the preparation of a reagent useful for the detection of Apoprotein A-1 in a biological fluid, said reagent comprising antibody to Apoprotein A-1 bound to 25 to 30 molecules of fluorescein isothiocyanate, said method comprising reacting fluorescein isothiocyanate and said antibody at a molar ratio of about 130:1 for about 30 to 40 minutes at a temperature of about 37° C. to thereby form said reagent.
25. In an assay method for determining the presence of a ligand in a biological fluid in an aqueous medium which comprises combining a reagent, said biological fluid suspected of containing said ligand and a buffer under conditions which permit a ligand-antibody binding reaction, the improvement comprising employing a reagent comprising:
   an antibody to said ligand bound to more than 10 dye molecules through an isothiocyanate group on the dye molecule and determining the amount of absorbance of photons in said medium.
26. The assay method of claim 25 wherein the antibody of said reagent is bound to 15 to 40 of said dye molecules.

27. The assay of method of claim 26 wherein the antibody of said reagent is bound to 20 to 35 of said dye molecules.

28. The assay method of claim 25 wherein the ligand to be detected is Apoprotein A-1.

29. The assay method of claim 25 wherein said dye molecules has molar extinction coefficient of at least 50,000.

30. The assay method of claim 29 wherein said dye molecule has molar extinction coefficient of 50,000 to 220,000.

31. The assay method of claim 30 wherein said dye molecule are selected from the group consisting of isothiocyanate derivatives of aminofluorescein and aminophthalocyanines, Chicago Sky Blue and Evans Blue.

32. The assay method of claim 31 wherein said dye molecule is fluorescein isothiocyanate.

33. The assay method of claim 25 comprising:
(a) reacting said ligand in said biological fluid and said reagent to thereby form a first complex of said ligand bound to said reagent through said antibody;
(b) adding to said first complex a solid phase support bound to antibody to said ligand;
(c) allowing said solid phase support bound to antibody to said ligand to react with said first complex to thereby form a second complex and a solution containing unreacted reagent;
(d) separating said second complex from said solution; of photons of said solution containing unreacted reagent; and
(f) comparing said amount with the amount of absorbance of a standard solution containing a known amount of said ligand.

34. The assay method of claim 33 wherein the ligand to be detected is Apoprotein A-1.

35. The assay method of claim 33 wherein said dye molecule is fluorescein isothiocyanate.

36. The assay method of claim 25 comprising:
(a) reacting said ligand in said biological fluid with a solid phase support bound to an antibody to said ligand to thereby form a first complex;
(b) adding said reagent to said first complex;
(c) allowing said reagent and said first complex to react to thereby form a second complex and a solution containing unreacted reagent;
(d) separating said second complex from said solution;
(e) determining the amount of absorbance of photons of said solution containing unreacted reagent; and
(f) comparing said amount with the amount of absorbance of a standard solution containing a known amount of said ligand.

37. The assay method of claim 36 wherein the ligand to be detected is Apoprotein A-1.

38. The assay method of claim 36 wherein said dye molecule is fluorescein isothiocyanate.

* * * * *